United States Patent [19]

Mukaiyama et al.

[11] 4,276,217

[45] Jun. 30, 1981

[54] METHOD FOR PRODUCING 1,5-DIMETHYL-6,8-DIOXABICYCLO[3.2.-1]OCTANE

[75] Inventors: Teruaki Mukaiyama, Tokyo; Yoji Sakito, Ibaraki, both of Japan

[73] Assignee: Sumitomo Chemical Company, Limited, Osaka, Japan

[21] Appl. No.: 170,955

[22] Filed: Jul. 21, 1980

[30] Foreign Application Priority Data

Jul. 31, 1979 [JP] Japan .................................. 54/98361
Jul. 31, 1979 [JP] Japan .................................. 54/98362

[51] Int. Cl.$^3$ ........................................... C07D 317/44
[52] U.S. Cl. .............................. 260/340.9 R; 548/353; 568/857
[58] Field of Search ...................... 260/340.7, 340.9 R

[56] References Cited

U.S. PATENT DOCUMENTS

| | | | |
|---|---|---|---|
| 3,647,823 | 3/1972 | Isard et al. ................... | 260/340.9 R |
| 3,755,365 | 8/1973 | Fentiman et al. ............. | 260/340.9 R |
| 3,901,919 | 8/1975 | Woodward ..................... | 260/340.7 |

FOREIGN PATENT DOCUMENTS 1096342  6/1955  France ................................. 260/340.9

OTHER PUBLICATIONS

Hicks et al., J. C. S. Chem. Comm., 869–870 (1976).
Ohrui et al., Agr. Biol. Chem., 40 (11), 2267–2270 (1976).
Mori, Tetrahedron, vol. 31, 1381–1384 (1975).

*Primary Examiner*—Ethel G. Love
*Attorney, Agent, or Firm*—Stevens, Davis, Miller & Mosher

[57] ABSTRACT

A method for producing optically active or racemic 1,5-dimethyl-6,8-dioxabicyclo[3.2.1]octane characterized by reducing optically active or racemic 2-hydroxy-2,6-dimethyl-6-heptenal and oxidizing the resulting optically active or racemic 2,6-dimethyl-6-heptene-1,2-diol, and optically active or racemic 2,6-dimethyl-6-heptene-1,2-diol.

7 Claims, No Drawings

METHOD FOR PRODUCING 1,5-DIMETHYL-6,8-DIOXABICYCLO[3.2.1]OCTANE

The present invention relates to a method for producing 1,5-dimethyl-6,8-dioxabicyclo[3.2.1]octane.

More particularly, it relates to a method for producing optically active or racemic 1,5-dimethyl-6,8-dioxabicyclo[3.2.1]octane (hereinafter referred to as frontalin) characterized by oxidizing optically active or racemic 2,6-dimethyl-6-heptene-1,2-diol and a method for producing optically active or racemic frontalin by reducing optically active or racemic 2-hydroxy-2,6-dimethyl-6-heptenal and oxidizing the resulting optically active or racemic 2,6-dimethyl-6-heptene-1,2-diol.

Frontalin is an aggregation pheromone of several kinds of insect belonging to genus Dendroctonus such as *Dendroctonus Frontalis* Zimmerman. The aggregation pheromone acts on a certain kind of organisms to gather then together. It is therefore possible to gather insects together to one place by using aggregation pheromone and to kill them, or it is possible to disturb breeding by scattering aggregation pheromone in air thereby preventing insects from gathering together. Aggregation pheromone is therefore expected as a novel insecticide which is different in type from the conventional insecticides.

Frontalin has a unique action on several kinds of insect belonging to genus Dendroctonus. It is well known that even the racemate of frontalin has a biological activity, but that, as to the two optical isomers of frontalin, only the optical isomer of S-configuration has the activity [Science, 192, 896 (1976)]. Consequently, the development of a method for producing optically active frontalin has a very important significance.

The present invention provides a novel method for producing optically active frontalin by using optically active 2-hydroxy-2,6-dimethyl-6-heptenal. According to the method of the present invention, further, racemic frontalin can be produced by using racemic 2-hydroxy-2,6-dimethyl-6-heptenal.

That is, (S)-frontalin, (R)-frontalin and racemic frontalin can be produced in a novel and industrially advantageous manner from (S)-2-hydroxy-2,6-dimethyl-6-heptenal, (R)-2-hydroxy-2,6-dimethyl-6-heptenal and racemic 2-hydroxy-2,6-dimethyl-6-heptenal, respectively.

In carrying out the present invention (S)-2-hydroxy-2,6-dimethyl-6-heptenal, a starting material, can be produced from the aminal of (S)-6-methyl-6-heptene-2-one-1-al, for example, as shown in the reference examples. Both (R)-2-hydroxy-2,6-dimethyl-6-heptenal and racemic 2-hydroxy-2,6-dimethyl-6-heptenal can be produced in the same manner.

The present invention will be illustrated hereinafter in more detail.

Method A:

Production of 2,6-dimethyl-6-heptene-1,2-diol

In this method, 2,6-dimethyl-6-heptene-1,2-diol is produced by the reduction of 2-hydroxy-2,6-dimethyl-6-heptenal. As reducing agents for reduction, the common ones which can reduce a carbonyl group without acting on a double bond, for example lithium aluminum hydride, sodium borohydride, diisobutyl aluminum hydride and lithium borohydride, may be used. Solvents used for reduction vary with the kind of reducing agent, but the common ones used for the reducing agent will do. For example, ether (e.g. diethyl ether), tetrahydrofuran and the like are used for reduction with lithium aluminum hydride or lithium borohydride; ethanol, diglyme and the like for reduction with sodium borohydride; and benzene, toluene, ether (e.g. diethyl ether), tetrahydrofuran and the like for reduction with diisobutyl aluminum hydride.

In carrying out this reaction, the reaction temperature is within a range of $-20°$ C. to the boiling point of the solvent, and the reaction time is within a range of 10 minutes to 2 hours. The amount of reducing agent is 1.0 to 5.0 equivalents based on 1 equivalent of 2-hydroxy-2,6-dimethyl-6-heptenal. Both the optical isomers and the racemate of 2,6-dimethyl-6-heptene-1,2-diol thus obtained are novel compounds.

Method B:

production of 1,5-dimethyl-6,8-dioxabicyclo[3.2.1]octane

In this method, 1,5-dimethyl-6,8-dioxabicyclo[3.2.1]octane (frontalin) is produced through 6-methyl-6,7-dihydroxyheptane-2-one by the oxidation of 2,6-dimethyl-6-heptene-1,2-diol produced by Method A. As the oxidizing agent, ozone is used which acts to cause the oxidative cleavage of a double bond without acting on a hydroxyl group. As the solvent used for oxidation, those which are used for the common ozone oxidation, for example methylene chloride, chloroform, ethyl acetate n-hexane, methanol, ethanol, petroleum ether, and the mixture thereof may be used.

The ozonide obtained by the oxidation of 2,6-dimethyl-6-heptene-1,2-diol with ozone is then reduced, usually in the same solvent as used in the oxidation, with a reagent commonly used for the reduction of ozonides for example dimethyl sulfide, triphenyl phosphine or the like. By this treatment, frontalin can be obtained at one step from 2,6-dimethyl-6-heptene-1,2-diol through 6-methyl-6,7-dihydroxyheptane-2-one, which may be considered as an intermediate produced by the oxidation of said 1,2-diol, and the intramolecular acetalization thereof.

In carrying out this reaction, the reaction temperature and time are $-80°$ to $0°$ C. and less than 10 hours, respectively, for the oxidation of 2,6-dimethyl-6-heptene-1,2-diol with ozone, and they are $-80°$ to $30°$ C. and 10 minutes to 2 hours, respectively, for the reduction of the ozonide. The amount of ozone, an oxidizing agent, is 1.0 to 1.5 equivalent based on 1 equivalent of 2,6-dimethyl-6-heptene-1,2-diol, and the amount of the reagent for reducing (decomposing) the ozonide is 1.0 to 5.0 equivalents based on 1 equivalent of the ozonide.

The present invention will be illustrated in more detail with reference to the following examples, which are not however to be interpreted as limiting the invention thereto.

REFERENCE EXAMPLE 1

S-2-(anilinomethyl)pyrrolidine (490 mg) and methyl hydroxymethoxyacetate (351 mg) were dissolved in benzene, and the resulting solution was refluxed for 30 minutes with azeotropic removing of produced water. The solvent was then removed under reduced pressure. The residue obtained was dissolved in tetrahydrofuran (25 ml), and anhydrous magnesium chloride (291 mg) was added thereto, followed by refluxing for 10 minutes. After cooling to $-100°$ C., an ether solution containing 4-methyl-4-pentenylmagnesium bromide of 1.5 times by equivalent based on said pyrrolidine was added thereto. Thereafter, an aqueous ammonium chloride-saturated solution was added to the reaction solution which was then raised to room temperature and extracted with ether.

The ether layer was washed with an aqueous sodium chloride-saturated solution and dried over sodium sulfate. The solvent was removed under reduced pressure, and the residue obtained was purified by column chromatography on alumina to obtain 525 mg of 2-(5-hexenoyl)-3-phenyl-1,3-diazabicyclo[3.3.0]octane.

REFERENCE EXAMPE 2

2-(5-Methyl-5-hexenoyl)-3-phenyl-1,3-diazabicyclo[3.3.0]octane (528 mg) obtained in Reference Example 1 was dissolved in ether (10 ml). The resulting solution was cooled to −75° C., and to the solution was added an ether solution containing methylmagnesium bromide of 1.5 times by equivalent based on said octane.

An aqueous ammonium chloride-saturated solution was added to the reaction solution which was then raised to room temperature and separated into aqueous and ether layers. The ether layer was cooled to 0° C., and a 2% hydrochloric acid (17 ml) was added thereto, followed by reaction for 2.5 hours. The ether layer was separated, and the aqueous layer was extracted with ether. The ether layers were combined, washed with an aqueous sodium chloride-saturated solution and dried over sodium sulfate.

Ether was removed under reduced pressure to obtain 270 mg of (S)-2-hydroxy-2,6-dimethyl-6-heptenal.

REFERENCE EXAMPLE 3

5-(S)-2-Acetyl-3-phenyl-1,3-diazabicyclo-[3.3.0]octane (643 mg) was dissolved in ether (15 ml). The resulting solution was cooled to −73° C., and to the solution was added an ether solution containing 4-methyl-4-pentenylmagnesium bromide of 1.5 times by equivalent based on said octane. Thereafter, an aqueous ammonium chloride-saturated solution was added to the reaction solution which was then raised to room temperature and separated into aqueous and ether layers. The ether layer was cooled to 0° C., and a 2% hydrochloric acid (30 ml) was added, followed by reaction for 2.5 hours. The ether layer was separated, and the aqueous layer was extracted with ether. The ether layers were combined, washed with an aqueous sodium chloride-saturated solution and dried over sodium sulfate. Ether was removed under reduced pressure to obtain 435 mg of (R)-2-hydroxy-2,6-dimethyl-6-heptenal.

REFERENCE EXAMPLE 4

(±)-2-Acetyl-3-phenyl-1,3-diazabicyclo-[3.3.0]octane (514 mg) was dissolved in ether (15 ml). The resulting solution was cooled to −73° C., and to the solution was added an ether solution containing 4-methyl-4-pentenylmagnesium bromide of 1.5 times by equivalent based on said octane. Thereafter, an aqueous ammonium chloride-saturated solution was added to the reaction solution which was then raised to room temperature and separated into aqueous and ether layers. The ether layer was cooled to 0° C., and a 2% hydrochloric acid (30 ml) was added thereto, followed by reaction for 2.5 hours. The ether layer was separated, and the aqueous layer was extracted with ether. The ether layers were combined, washed with an aqueous sodium chloride-saturated solution and dried over sodium sulfate. Ether was removed under reduced pressure to obtain 348 mg of (±)-2-hydroxy-2,6-dimethyl-6-heptenal.

EXAMPLE 1

(S)-2-Hydroxy-2,6-dimethyl-6-heptenal (270 mg) obtained in Reference Example 2 was dissolved in ethanol (5 ml), and sodium borohydride (33 mg) was added thereto, followed by reaction at 0° C. for 30 minutes. Water was added to the reaction solution which was then extracted with methylene chloride. The extract was dried over sodium sulfate, and the solvent was removed under reduced pressure. The residue obtained was purified by column chromatography on silica gel to obtain 194 mg of (S)-2,6-dimethyl-6-heptene-1,2-diol.

NMR peak: $\delta$ (ppm)=1.1 (3H, s), 1.4 (4H, m), 1.7 (3H, s), 1.9 (2H, m), 3.3 (2H, s), 3.5 (2H, broad singlet), 4.5 (2H, s).

Specific rotation: $[\alpha]_D$−2.0° (c=0.85, methylene chloride).

EXAMPLE 2

(R)-2-Hydroxy-2,6-dimethyl-6-heptenal (430 mg) obtained in Reference Example 3 was dissolved in ethanol (10 ml), and sodium borohydride (57 mg) was added thereto, followed by reaction at 0° C. for 30 minutes.

The subsequent operation was carried out in the same manner as in Example 1 to obtain 314 mg of (R)-2,6-dimethyl-6-heptene-1,2-diol.

NMR peaks were the same as in Example 1, and the specific rotation: $[\alpha]_D$+2.4° (c=1.12, methylene chloride).

EXAMPLE 3

(S)-2,6-Dimethyl-6-heptene-1,2-diol (481 mg) obtained in Example 1 was dissolved in methylene chloride (5 ml), and the resulting solution was cooled to −70° C., followed by reaction with ozone. After the material was no longer detectable (confirmed by thin layer chromatography), dimethyl sulfide (0.8 ml) was added, and the reaction solution was raised to room temperature, followed by reaction for 2 hours. The solvent was removed under atmospheric pressure, and the residue obtained was purified by column chormatography on alumina to obtain 391 mg of (S)-frontalin. The optical purity was 84% as calculated from the specific rotation: $[\alpha]_D$−45.5° (c=1.75, ether).

EXAMPLE 4

Using (R)-2,6-dimethyl-6-heptene-1,2-diol obtained in Example 2, operation was carried out in the same manner as in Example 3 to obtain (R)-frontalin. The optical purity was 100% as calculated from the specific rotation: $[\alpha]_D$+54.3° (c=3.38, ether).

EXAMPLE 5

(±)-2-Hydroxy-2,6-dimethyl-6-heptenal (387 mg) obtained in Reference Example 4 was dissolved in ether (10 ml), and lithium aluminum hydride (65 mg) was added thereto, followed by reaction at room temperature for 15 minutes. An excess of lithium aluminum hydride was quenched with an aqueous sodium sulfate-saturated solution. The ether layer was dried over sodium sulfate, and the solvent was removed under reduced pressure. The residue obtained was purified by column chromatography on silica gel to obtain 280 mg of (±)-2-dimethyl-6-heptene-1,2-diol.

EXAMPLE 6

(±)-2,6-Dimethyl-6-heptene-1,2-diol (418 mg) was dissolved in ethyl acetate (5 ml), and the resulting solution was cooled to −50° C., followed by reaction with ozone. After the material was no longer detectable (confirmed by thin layer chromatography), dimethyl sulfide (0.7 ml) was added, and the reaction solution was raised to room temperature, followed by reaction for 2 hours. The solvent was removed under atmospheric pressure, and the residue obtained was purified by column chromatography on alumina to obtain 310 mg of (±)-frontalin.

What is claimed is:

1. A process for producing an optically active or a racemic 1,5-dimethyl-6,8-dioxabicyclo[3.2.1]octane, which comprises reacting an optically active or a racemic 2,6-dimethyl-6-hepten-1,2-diol with ozone at a temperature of −80° to 0° C. within 10 hours in an inert solvent, to obtain the optically active or racemic ozonide and reductive working up said ozonide with a reducing agent at a temperature of −80° to 30° C. within the range of 10 minutes to 2 hours in an inert solvent.

2. The process according to claim 1, wherein ozone is used in an amount of 1.0 to 1.5 equivalents based on the optically active or racemic 2,6-dimethyl-6-heptene-1,2-diol.

3. The process according to claim 1, wherein the reducing agent is dimethyl sulfide or triphenylphosphine.

4. The process according to claim 1, wherein the reducing agent is used in an amount of 1.0 to 5.0 equivalents based on the ozonide.

5. The process according to claim 1, wherein the optically active or racemic 2,6-dimethyl-6-heptene-1,2-diol is produced by reducing an optically active or racemic 2-hydroxy-2,6-dimethyl-6-heptenal with an reducing agent in an inert solvent as a temperature of −20° C. to the boiling point of the used solvent within the range of 10 minutes to 2 hours.

6. The process according to claim 5, wherein the reducing agent is lithium aluminum hydride, sodium borohydride, diisobutyl aluminium hydride or lithium borohydride.

7. The process according to claim 5, wherein the reducing agent is used in an amount of 1.0 to 5.0 equivalents based on the optically active or racemic 2-hydroxy-2,6-dimethyl-6-heptenal.

* * * * *